United States Patent [19]

Martel et al.

[11] 4,421,928
[45] Dec. 20, 1983

[54] 4-METHYL-3-FORMYL-PENTANOIC ACID ESTERS

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 352,259

[22] Filed: Feb. 25, 1982

[30] Foreign Application Priority Data

Feb. 26, 1981 [FR] France ................................ 81 03832

[51] Int. Cl.³ .................. C07C 69/708; C07C 69/716
[52] U.S. Cl. ...................................... 560/177; 560/184
[58] Field of Search ....................... 560/184, 177, 219; 562/577, 586

[56] References Cited

U.S. PATENT DOCUMENTS 4,217,300  8/1980  Lantzsch .............................. 560/219

Primary Examiner—Natalie Trousof
Assistant Examiner—L. Hendriksen
Attorney, Agent, or Firm—Hammond & Littell, Weissenberger and Muserlian

[57] ABSTRACT

Novel 4-methyl-3-formyl-pentanoic acid derivative of the formula

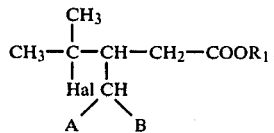

wherein Hal is a halogen, $R_1$ is alkyl of 1 to 12 carbon atoms and A and B are =O or A is halogen and B is —$OR_2$ and $R_2$ is alkyl of 1 to 12 carbon atoms, their preparation and their use as intermediates.

5 Claims, No Drawings

4-METHYL-3-FORMYL-PENTANOIC ACID ESTERS

OBJECTS OF THE INVENTION

It is an object of the invention to provide the novel compounds of formula I and a process for their preparation.

It is another object of the invention to provide novel processes for the preparation of valuable industrial compounds and novel intermediates.

These and other objects and advantages of the invention will become obvious from the following detailed description.

THE INVENTION

The novel derivatives of the invention are compounds of the formula

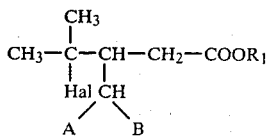

wherein Hal is a halogen, $R_1$ is alkyl of 1 to 12 carbon atoms and A and B are =O or A is halogen and B is $-OR_2$ and $R_2$ is alkyl of 1 to 12 carbon atoms.

The preferred halogens are chlorine or bromine and $R_1$ is preferably methyl, ethyl, n-propyl, isopropyl, butyl, isobutyl or pentyl. $R_2$ is preferably methyl, ethyl, n-propyl, isopropyl, butyl, isobutyl or pentyl.

Preferred compounds of formula I have a formula selected from the group consisting of

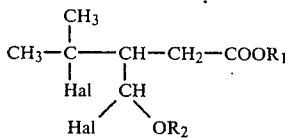

and

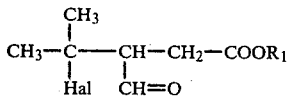

wherein Hal, $R_1$ and $R_2$ have the above definition. Especially preferred compounds of formula I are those wherein Hal is chlorine and those wherein $R_1$ is methyl.

The novel process of the invention for the preparation of a compound of formula I comprises reacting a compound of the formula

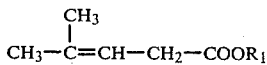

wherein $R_1$ has the above definition with a compound of the formula

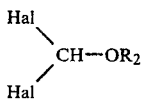

wherein Hal and $R_2$ have the above definition in the presence of an acid agent to obtain the corresponding compound of formula $I_A$ and optionally reacting the latter with a hydrolysis agent to obtain the corresponding compound of formula $I_B$.

The acid agent is preferably an inorganic acid such as sulfuric acid or hydrochloric acid although Lewis acids may also be used. Examples of suitable Lewis acids are aluminum trichloride, tin tetrachloride, titanium tetrachloride, ferric chloride and zinc dichloride.

In a preferred embodiment of the process of the invention, $R_1$ and $R_2$ are the same. The reaction of compounds of formulae II and III is effected at a low temperature of $-80°$ to $0°$ C., preferably $-10°$ to $-50°$ C. and the reaction is effected in methylene chloride or another inert organic solvent. The preferred hydrolysis agent is water and the reaction is effected at $-50°$ to $10°$ C., preferably about $0°$ C.

The compounds of formula I have a very great industrial interest and may be prepared by a simple and very rapid process beginning from compounds of formula II. As shown in the examples, it is possible to form the compounds of formula $I_B$ from the compounds of formula II without separating the compounds of formula $I_A$. The products of formula $I_B$ are easily separated and purified and the compounds of formula $I_A$ or $I_B$ may be recovered by crystallization or distillation.

The compounds of formula I can be rapidly transformed by very simple reactions using inexpensive reactants into products having a great industrial interest which permits the preparation of a large number of pesticide products of cis or trans cyclopropane carboxylic acid such as described in French Pat. No. 2,185,612.

There was not known before the present invention a process for the preparation of precursers of cis or trans cyclopropane carboxylic acid esters. The industry which wishes to produce esters of the cis and the trans series had to have two separate operating units while the process of the present invention allows one to use the same installations on a large scale for the production of esters of cis or trans acids. It is unexpected since it was not known that a process would permit access at the same time to the cis series and the trans series which is of great industrial interest because it reduces the production costs of the products to be prepared. The use of the products of formula I provide a solution to an industrial problem which had not been solved before.

The use of the products of formula I to prepare intermediates for the industrial synthesis of derivatives of cis or trans cyclopropane carboxylic acids is also a part of the present invention.

One process of the invention comprises reacting a compound of formula $I_A$ with an acid hydrolysis agent to obtain a compound of the formula

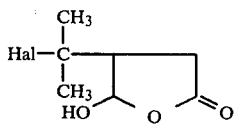

wherein Hal is a halogen which compounds are described in French Pat. No. 2,458,533 as intermediates for the preparation of the internal hemiacylal of 2,2-dimethyl-3-formylcyclopropane-l-carboxylic acid of the formula

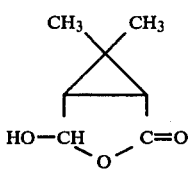

which is a known industrial product useful as an intermediate for derivatives of cis cyclopropane carboxylic acid such as described in optically active form in French Pat. No. 1,580,474.

Another process of the invention comprises reacting a compound of formula $I_A$ with an alcohol of the formula

    V wherein $R_2$ has the above definition to obtain a compound of the formula

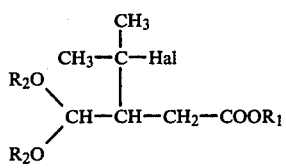    VI and treating the latter successively with a base, a saponification agent and then a hydrolysis agent to obtain a compound of the formula

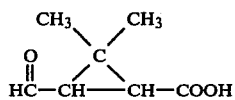    VII which is trans 2,2-dimethyl-3-formyl-cyclopropane-1-carboxylic acid described in U.S. Pat. No. 4,024,163.

A further process of the invention comprises reacting a compound of formula $I_B$ which an alcohol of formula V to obtain the corresponding compound of formula VI which can be converted as above to the compound of formula VII.

In preferred embodiments of the said latter three processes, the hydrolysis agent leading to a compound of formulae IV and VII is hydrochloric acid or sulfuric acid or other strong acids in aqueous solution. The reaction with the alcohol of formula V is effected between 5° C. and room temperature and is selected depending on the desired value of $R_2$. The base is concentrated aqueous sodium hydroxide or other strong base in a non-aqueous medium preferably in the presence of a phase transfer catalyst. The saponification agent may be an alkali metal hydroxide or alkaline earth metal hydroxide in aqueous alcohol. The reaction of the alcohol and the compound of formula $I_B$ is effected in the presence of an acid catalyst such as p-toluene sulfonic acid.

The compounds of formula VI are novel compounds and are a part of the invention and are useful intermediates for the preparation of the acids of formula VII.

In the following examples there are described several preferred embodiments to illustrate the invention. However, it is to be understood that the invention is not intended to be limited to the specific embodiments.

EXAMPLE 1

Methyl 4-chloro-4-methyl-3-formyl-pentanoate

STEP A: Methyl 3-(methoxychloromethyl)-4-chloro-4-methyl-pentanoate

A solution of 1.3 ml of a α-dichloromethyl methyl ether in 5 ml of methylene chloride was added at −35° C. to a mixture of 1.4 g of aluminum trichloride and 10 ml of methylene chloride and then a solution of 1 g of methyl 4-methyl-3-pentenoate in 6 ml of methylene chloride was added at −40° to −50° C. to the resulting suspension. The mixture was stirred for one hour while allowing the temperature to return to −10° to 0° C. to obtain a methylene chloride solution of methyl 3-(methoxychloromethyl)-4-chloro-4-methyl-pentanoate.

STEP B: Methyl 4-chloro-4-methyl-3-formyl-pentanoate

The solution of Step A was poured into an iced aqueous sodium bicarbonate solution and the mixture was extracted with methylene chloride. The organic phase was evaporated to dryness and the residue was chromatographed over silica gel. Elution with a 4-1 hexane-ethyl acetate mixture yielded 600 mg of methyl 4-chloro-4-methyl-3-formyl-pentanoate which crystallized at −20° C.

NMR Spectrum (deuterochloroform)

Peaks at 1.65 and 1.7 ppm (hydrogens of geminal methyls); at 10 ppm

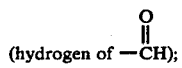

(hydrogen of —CH);

at 3.2 to 3.4 ppm

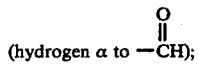

(hydrogen α to —CH);

at 2.33 to 2.95 ppm (hydrogen α to ester group); at 3.72 ppm

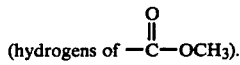

(hydrogens of —C—OCH₃).

EXAMPLE 2

4-(2-chloro-prop-2-yl)-tetrahydrofuran-5-ol-2-one

A solution of Step A of Example 1 was poured into a mixture of ice and water and the mixture was stirred at 0° to 10° C. for one hour and was extracted with methylene chloride. The organic phase was washed with dilute hydrochloric acid solution, dried over sodium sulfate and evaporated to dryness under reduced pressure at not more than 20°∼25° C. The 1.66 g of oil residue were immediately dissolved in 20 ml of acetone and 20 ml of N aqueous hydrochloric acid were added thereto at 20° C. The mixture was stirred at 20°-25° C. for 20 hours and was diluted with water and extracted with methylene chloride. The organic phase was evaporated to dryness to obtain 1.4 g of a crystaline gum which was empasted with petroleum ether (b.p.=40°-70° C.) to obtain 1.03 g of 4-(2-chloro-prop-2-yl)-tetrahydrofuran- 5-ol-2-one melting at 83° C. and which was identical to the product of Example 5 of French Pat. No. 2,458,533.

EXAMPLE 3

Trans 2,2-dimethyl-3-formyl-cyclopropane-carboxylic acid

STEP A: Methyl 4-chloro-4-methyl-3-dimethoxymethyl-pentanoate

A mixture of 5 g of the product of Example 1, 50 ml of methanol and 50 mg of p-toluene sulfonic acid was stirred at 20° C. for one hour and was then poured into aqueous sodium bicarbonate solution. The mixture was extracted with chloroform and evaporated to dryness to obtain 4-chloro-4-methyl-3-dimethoxymethyl-pentanoate as the fraction boiling at 62° C. at 0.05 mm Hg.

NMR Spectrum (deuterochloroform)

Peaks at 1.61 and 1.62 ppm (hydrogens of geminal methyls); at 4.47–4.51 ppm (hydrogens of acetal); at 3.34–3.4 ppm (hydrogens of dimethoxy of acetal); at 3.7 ppm

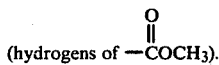
(hydrogens of —COCH$_3$).

STEP B: Methyl (R,S) trans 2,2-dimethyl-3-dimethoxymethyl-cyclopropane-1-carboxylate A mixture of 716 mg of the product of Step A, 7 ml of methylene chloride, 14 ml of a 50% aqueous sodium hydroxide solution and 70 mg of triethylbenzylammonium chloride was stirred at 20°–25° C. for 24 hours and was then poured into an aqueous saturated monosodium phosphate solution. The mixture was extracted with benzene and the organic phase was dried over sodium sulfate, filtered and evaporated to dryness under reduced pressure. The residue was chromatographed over silica gel and was eluted with a 95-5 benzene-ethyl acetate mixture to obtain 494 mg of methyl (R,S) trans 2,2-dimethyl-3-dimethoxymethyl-cyclopropane-1-carboxylate.

STEP C: Trans 2,2-dimethyl-3-formyl-cyclopropane-1-carboxylic acid 10 ml of 2N aqueous sodium hydroxide solution were added to a solution of 1 g of the product of Step B in 20 ml of methanol and the mixture was refluxed for 2 hours and then cooled. The reaction mixture was acidified to a pH of 1 by addition of 6N aqueous hydrochloric acid and the mixture stood at 20° C. for one hour. The mixture was diluted with water and was extracted with methylene chloride. The organic phase was dried and evaporated to dryness to obtain trans 2,2-dimethyl-3-formyl-cyclopropane-1-carboxylic acid.

EXAMPLE 4

Trans 2,2-dimethyl-3-formyl-cyclopropane-1-carboxylic acid

STEP A: Methyl 4-chloro-4-methyl-3-dimethoxymethyl-pentanoate

The solution of Step A of Example 1 was added to methanol at a low temperature and the mixture was stirred at 5°–10° C. for 3 hours and was poured into aqueous sodium bicarbonate solution. The mixture was filtered and the decanted aqueous phase was extracted with methylene chloride. The organic phase was washed with aqueous sodium bicarbonate solution and evaporated to dryness under reduced pressure to obtan 11 g of residue. The latter was chromatographed over silica gel and was eluted with a 9-1 petroleum ether (b.p.=40°–70° C.)-ethyl acetate mixture to obtain 8.66 g of methyl 4-chloro-4-methyl-3-dimethoxymethyl-pentanoate with a boiling point of 62° C. at 0.05 mm Hg which was identical to the product of Step A of Example 3.

STEP B: Trans 2,2-dimethyl-3-formyl-cyclopropane-1-carboxylic acid

Using the procedure of Steps B and C of Example 3, the product of Step A was reacted to obtain trans 2,2-dimethyl-3-formyl-cyclopropane-1-carboxylic acid.

Various modifications of the products and process of the invention may be made without departing from the spirit or scope thereof and it is to be understood that the invention is to be limited only as defined in the appended claims.

What we claim is:

1. A compound of the formula

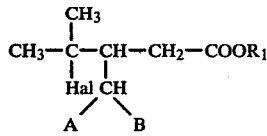

I wherein Hal is a halogen, R$_1$ is 1 to 12 carbon atoms and A and B are =O or A is halogen and B is OR$_2$ and R$_2$ is alkyl of 1 to 12 carbon atoms.

2. A compound of claim 1 wherein A is halogen and B is —OR$_2$.

3. A compound of claim 1 wherein A and B form =O.

4. A compound of claim 1 or 2 or 3 wherein Hal is chlorine.

5. A compound of claim 1 or 2 or 3 or 4 wherein R$_1$ is methyl.

* * * * *